United States Patent [19]

Kochanowski

[11] Patent Number: 5,128,374
[45] Date of Patent: Jul. 7, 1992

[54] USE OF CALCIUM CITRATE MALATE FOR THE TREATMENT OF OSTEOPOROSIS AND RELATED DISORDERS

[75] Inventor: Barbara A. Kochanowski, West Chester, Ohio

[73] Assignee: The Procter & Gamble Company, Cincinnati, Ohio

[21] Appl. No.: 590,314

[22] Filed: Sep. 27, 1990

Related U.S. Application Data

[63] Continuation of Ser. No. 355,076, May 18, 1989, abandoned, which is a continuation of Ser. No. 091,006, Aug. 28, 1987, abandoned.

[51] Int. Cl.⁵ .............................................. A61K 31/19
[52] U.S. Cl. .................................... 514/574; 514/836; 514/873
[58] Field of Search ................. 514/557, 574, 836, 873

[56] References Cited

U.S. PATENT DOCUMENTS

| | | | |
|---|---|---|---|
| 4,551,342 | 11/1985 | Nakel et al. | 426/548 |
| 4,722,847 | 2/1988 | Heckert | 426/74 |

FOREIGN PATENT DOCUMENTS

| | | |
|---|---|---|
| 208362 | 1/1987 | European Pat. Off. |
| 4384 | 10/1966 | France |
| 2219778 | 9/1974 | France |
| 548767 | 1/1979 | Japan |
| 5697248 | 8/1981 | Japan |
| 5931710 | 2/1984 | Japan |
| 8604814 | 8/1986 | PCT Int'l Appl. |
| 8604815 | 8/1986 | PCT Int'l Appl. |
| 193065 | 1/1938 | Switzerland |

OTHER PUBLICATIONS

L. Nilas et al., "Calcium Supplementation and Postmenopausal Bone Loss", 289 British Medical Journal 1103 (1984).

Spencer et al., "NIH Consensus Conference: Osteoporosis-Factors Contributing to Osteoporosis", 116 J. Nutrition 316 (1986).

Gordan et al., "NIH Consensus Conference: Osteoporosis-Calcium and Osteoporosis", 116 J. Nutrition 319 (1986).

B. Riis et al., "Does Calcium Supplementation Prevent Postmenopausal Bone Loss?", 316 New Engand Journal of Medicine 173 (1987).

M. Sheikh et al., "Gastrointestinal Absorption of Calcium from Milk and Calcium Salts", 17 New England Journal of Medicine 532 (1987).

Pak, Chem. Abst. 106(3):12965p (1987).

Garrison et al., *The Nutrition Desk Reference*, (1985) pp. 58-59.

Riggs et al., "Involutional Osteoporosis", 314 *New England Journal of Medicine* (1986).

*Primary Examiner*—Richard I. Raymond
*Assistant Examiner*—Gary E. Hollinden
*Attorney, Agent, or Firm*—David L. Suter; Karen F. Clark; Jack D. Schaeffer

[57] ABSTRACT

Methods for building bone in a human or other animal subject, comprising administering to said subject a safe and effective amount of calcium citrate malate. The calcium citrate malate is preferably administered for at least about three months. A preferred method of the invention is for the treatment of osteoporosis. The calcium citrate malate comprises a complex or a mixture of calcium salts having a ratio of moles citrate to moles malate of from about 1:0.16 to about 1:13.5. The calcium citrate malate is preferably administered in an oral dosage form, containing pharmaceutically-acceptable carriers and excipients.

17 Claims, No Drawings

USE OF CALCIUM CITRATE MALATE FOR THE TREATMENT OF OSTEOPOROSIS AND RELATED DISORDERS

This is a continuation of application Ser. No. 07/355,076, filed on May 18, 1989, now abandoned, which was a continuation of application Ser. No. 091,006, filed on Aug. 28, 1987, abandoned.

BACKGROUND OF THE INVENTION

This invention relates to methods of building bone in humans and other animals, i.e., for the treatment of osteoporosis and related disorders. In particular, this invention relates to such methods of treatment by administration of certain calcium salts.

Calcium is the fifth most abundant element in the human body. It plays an important role in many physiological processes, including nerve and muscle functions. Not surprisingly, nutritional and metabolic deficiencies of calcium can have broad-ranging adverse effects. Since about 90% of the body's calcium is found in bone tissues, many of these adverse effects are manifested through deficiencies in the structure, function and integrity of the skeletal system.

The most common metabolic bone disorder is osteoporosis. Osteoporosis can be generally defined as the reduction in the quantity of bone, or the atrophy of skeletal tissue. In general, there are two types of osteoporosis: primary and secondary. "Secondary osteoporosis" is the result of an identifiable disease process or agent. However, approximately 90% of all osteoporosis cases is idiopathic "primary osteoporosis". Such primary osteoporosis includes postmenopausal osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures often occur, for example, in the wrist and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling occurs in a series of discrete pockets of activity in the bone, called "osteoclasts" and "osteoblasts". Osteoclasts (bone dissolving or resorbing cells) are responsible for the resorption of a portion of bone within the bone matrix, during the resorption process. After resorption, the osteoclasts are followed by the appearance of osteoblasts (bone forming cells), which then refill the resorbed portion with new bone.

In a healthy adult, the rate at which the osteoclasts and osteoblasts are formed maintains a balance of bone resorption and bone formation. However, in osteoporotics an imbalance in this remodeling process develops, resulting in loss of bone at a rate faster than the accretion of bone. This imbalance is much more severe, and occurs at a younger age, in osteoporotics as compared to healthy adults.

Many compositions and methods are described in the medical literature for the "treatment" of osteoporosis. Many of these compositions and methods attempt to either slow the loss of bone or to produce a net gain in bone mass. See, for example, R. C. Haynes, Jr. et al., "Agents affecting Calcification", *The Pharmacological Basis of Therapeutics*, 7th Edition (A. G. Gilman, L. S. Goodman et al., Editors, 1985); and G. D. Whedon et al., "An Analysis of Current Concepts and Research Interest in Osteoporosis", *Current Advances in Skeletogenesis* (A. Ornoy et al., Editors, 1985). Estrogen is often used to affect the metabolism of calcium. Treatments using fluoride have also been described. However, the utility of such agents may be limited, due to possible adverse side effects. See W. A. Peck, et al., *Physician's Resource Manual on Osteoporosis* (1987), published by the National Osteoporosis Foundation (incorporated by reference herein).

Nutritional therapies for osteoporosis have also been proposed. Many calcium-containing compounds and compositions have been described for use as nutritional supplements. Many commercial preparations are also available, typically containing calcium carbonate. Calcium chloride, calcium gluceptate, calcium gluconate, calcium lactate, calcium phosphate, calcium citrate, and other calcium salts have also been described for use in calcium supplements. The use of calcium citrate, for example, is described in French Patent 2,219,778, Monteau, published Sep. 27, 1974; and World Patent Publications 86/04814 and 86/04815, Pak et al., both published Aug. 28, 1986. Food supplements containing calcium citrate malate are described in Japanese Patent Document 56/97, 248, Kawai, published Aug. 5, 1981.

The utility of these known supplements varies. Unlike agents (such as estrogen) which affect the metabolism of bone, calcium nutritional supplements have been thought to merely provide a source for calcium (which may or may not be properly absorbed and metabolized). Indeed, the literature is bereft of any credible clinical data supporting the utility of any of these calcium supplements to actually treat osteoporosis (to actually build bone). See, for example, B. Riis et al., "Does Calcium Supplementation Prevent Postmenopausal Bone Loss?", 316 *New England J. of Medicine* 173–177 (1987); L. Nilas et al., "Calcium Supplementation and Postmenopausal Bone Loss", 289 *British Medical Journal* 1103–1106 (1984); and H. Spencer et al., "NIH Consensus Conference: Osteoporosis", 116 *Journal of Nutrition* 316–319 (1986).

It has now been discovered, however, that certain methods of treatment, involving the administration of mixtures of certain calcium salts, are surprisingly effective for the building of bone. In particular, as compared to nutritional regimens known in the art, these methods afford greater efficacy in the treatment of osteoporosis and related disorders.

SUMMARY OF THE INVENTION

The present invention provides methods for building bone in a human or other animal subject, comprising administering to said subject a safe and effective amount of calcium citrate malate. The calcium citrate malate comprises a complex or a mixture of calcium salts having a ratio of moles citrate to moles malate of from about 1:0.16 to about 1:13.5. A preferred calcium citrate malate for use in the methods of this invention has a molar composition of calcium:citrate:malate of about 6:2:3. The calcium citrate malate is preferably administered in an oral dosage form, containing pharmaceutically-acceptable carriers and excipients.

DESCRIPTION OF THE INVENTION

The methods of the present invention comprise the administration of calcium citrate malate to a human or other animal subject. Specific compounds and compositions to be used in these processes must, accordingly, be pharmaceutically-acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side affects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the duration of the treatment, the nature of concurrent therapy (if any), and the specific formulations employed.

Calcium Citrate Malate and Compositions

The methods of this invention involve administration of a mixture of calcium salts, herein "calcium citrate malate", comprising calcium salts of citric acid and malic acid. The calcium citrate malate may consist of a mixture of calcium citrate and calcium malate, a complex of calcium containing citrate and malate ligands, a mixture of a calcium salt with citric acid and malic acid, or combinations thereof. (Mixtures of a calcium salt and citric and malic acids may be used to form calcium citrate malate in situ, in a liquid dose form, or in the acid environment of the stomach of the subject to whom the mixture is administered.)

The molar ratio of citrate:malate is from about 1:0.16 to about 1:13.5, preferably from about 1:0.5 to about 1:4.5, more preferably from about 1:0.75 to about 1:3. A preferred calcium citrate malate has a molar citrate:malate ratio of about 1:1.5.

The ratio of moles calcium:total moles citrate plus malate is from about 1:0.2 to about 1:1.5, preferably from about 1:0.7 to about 1:0.9, more preferably about 1:0.83. Accordingly, the calcium citrate malate may contain other acid anions in addition to citrate and malate. Such anions may include, for example, carbonate, hydroxide, and mixtures thereof.

Preferably, the calcium citrate malate is neutral, comprised entirely of citrate and malate anions. Thus, preferably, the equivalents of calcium ($2 \times$ moles calcium) is about equal to the total number of equivalents of citrate ($3 \times$ moles citrate) plus malate ($2 \times$ moles malate). A preferred calcium citrate malate has a calcium:citrate:malate molar composition of about 6:2:3. Such a preferred calcium citrate malate is described in copending U.S. patent application Ser. No. 090,813 (Norwich Eaton Case N-499), Jacobs, "Novel Calcium Supplements", filed Aug. 28, 1987 (incorporated by reference herein).

The calcium citrate malate for use in the methods of this invention may be provided in solid or liquid dosage forms. Calcium citrate malate for use in solid forms may be made, for example, by first dissolving citric acid and malic acid, in the desired molar ratio, in water. Calcium carbonate may then be added to the solution, in such amount that the ratio of moles calcium to moles citrate and moles malate is as desired. Carbon dioxide will be evolved. The solution may then be dried (as by freeze drying or oven drying) to obtain the calcium citrate malate. Methods for making calcium citrate malate are described in the following documents (all incorporated by reference herein): European Patent Publication 208,362, Anastasia et al., published Jan. 14, 1987; Japanese Patent Specification SHO 56-97248, Kawai, published Aug. 5, 1981; and U.S. Pat. No. 4,722,847, Heckert, "Fruit Juice Beverages and Juice Concentrates Nutritionally Supplemented with Calcium", issued Feb. 2, 1988.

Various oral dosage forms of calcium citrate malate may be used in the present invention. Such dosage forms comprise a safe and effective amount of calcium citrate malate and a pharmaceutically-acceptable carrier. Preferably the pharmaceutically-acceptable carrier is present at a level of from about 0.1% to about 99%, preferably from about 0.1% to about 75%, by weight of the composition. Unit dosage forms (i.e., dosage forms containing an amount of calcium citrate malate suitable for administration in one single dose, according to sound medical practice) preferably contain from about 100 mg (milligrams) to about 1000 mg, preferably from about 100 mg to about 500 mg, more preferably from about 200 mg to about 300 mg of calcium (on an elemental basis).

Solid forms include tablets, capsules, granules and bulk powders. Aside from the calcium citrate malate, tablets may contain suitable binders, lubricants, diluents, disintegrating agents, coloring agents, flavoring agents, flow-inducing agents and melting agents. Liquid oral dosage forms include aqueous solutions, emulsions, suspensions, solutions and/or suspensions reconstituted from non-effervescent granules and effervescent preparations reconstituted from effervescent granules. Such liquid oral dosage forms may contain, for example, suitable solvents, preservatives, emulsifying agents, suspending agents, diluents, sweeteners, melting agents, and coloring and flavoring agents. A preferred liquid dosage form contains calcium citrate malate in a juice-containing beverage.

Specific examples of pharmaceutically-acceptable carriers and excipients that may be used to formulate oral dosage forms of the present invention are described in U.S. Pat. No. 3,903,297, Robert, issued Sep. 2, 1975, incorporated by reference herein. Techniques and compositions for making dosage forms useful in the methods of this invention are described in the following references, all incorporated by reference herein: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2d Edition. (1976).

METHODS OF TREATMENT

Specifically, the present invention provides a method for building bone in a human or other animal subject, comprising administering to said subject a safe and effective amount of calcium citrate malate for a period of time sufficient to achieve an increase in the net skeletal mass of said subject. As used herein, "building bone" refers to an increase in the net skeletal mass of the subject treated. The increase in mass may be in cortical bone, trabecular bone, or both. Preferably, the net skeletal mass is increased by at least about 0.5%, more preferably at least about 1%. "Administering" refers to any method which, in sound medical practice, delivers the calcium citrate malate used in this invention to the subject to be treated in such a manner so as to be effective in the building of bone. Preferably, the calcium citrate malate is administered orally.

Preferably, from about 175 milligrams to about 2000 milligrams of calcium (as elemental calcium) are administered to said subject, per day. More preferably, from about 250 milligrams to about 1500 milligrams, more preferably from about 500 milligrams to about 1000 milligrams, of calcium are administered, per day. The specific amount of calcium citrate malate to be administered depends upon the relative percentage weight of calcium in the particular calcium citrate malate employed.

The specific period of time sufficient to achieve an increase in the net skeletal mass of the subject may depend on a variety of factors. Such factors include, for example, the specific calcium citrate malate formulation employed, the amount of calcium citrate malate administered, the age and sex of the subject, the specific disorder to be treated, concomitant therapies employed (if any), the general physical health of the subject (including the presence of other disorders), the extent of bone loss in the individual, and the nutritional habits of the individual. Although the administration of even small quantities of calcium citrate malate may build bone, the net increase in bone mass may not be detectable for short periods of administration.

For the treatment of osteoporosis, the calcium citrate malate is preferably administered for at least about three months, preferably for at least about six months. Of course, such administration may be continued indefinitely, according to sound medical practice. Preferably the subject is treated until a net skeletal mass is obtained that is clinically determined to be above the fracture threshold for the subject. See, B. L. Riggs et al., "Involutional Osteoporosis" 314 *New England J. of Medicine* (1986), incorporated by reference herein.

The methods of this invention may be employed in the treatment of any of a variety of disorders in which the building of bone is desired. Thus, preferably, the human or other animal "subject" of the methods of this invention is "in need" of a method for building bone, i.e., the subject has a disorder for which building of bone would be advantageous according to sound medical practice. Such disorders include, for example, bone fractures and disorders typified by bone loss, such as osteoporosis (both primary and secondary forms).

A preferred method of this invention is for the treatment of osteoporosis. Such methods may include administration of calcium citrate malate alone, or in combination with other therapeutic agents. In particular, one method of this invention involves administration of calcium citrate malate as part of an "ADFR" regimen. Such a regimen, in general, comprises administration to the subject of a bone-cell activating agent (such as an inorganic phosphate); followed by administration of an osteoclast depressant, to inhibit bone resorption (such as a diphosphonate); followed by a "free" period during which osteoblast bone formation occurs. The entire cycle is preferably repeated. Such regimens, among those useful herein, are described in Belgian Patent Publication 902,307, Anderson et al., "Treatment of Osteoporosis", published Oct. 29, 1985 (incorporated by reference herein) and Belgian Patent Publication 902,308, Flora, "Treatment of Osteoporosis", published Oct. 29, 1985 (incorporated by reference herein). Preferably, in such regimens calcium citrate malate is administered during the free period. Kits to facilitate ADFR regimens are described in European Patent Specification 162,510. Uchtman, "Kit for Use in the Treatment of Osteoporosis", published Nov. 27, 1985 (incorporated by reference herein).

Another method of this invention involves administration of calcium citrate malate as part of a regimen comprising intermittent dosing of certain polyphosphonate compounds. Such methods comprise administration of the polyphosphonate followed by a "rest period". Such regimens, among those useful herein, are described in European Patent Specification 210,728, Flora et al., "Regimen for Treating Osteoporosis", published Feb. 4, 1987 (incorporated by reference herein). Preferably, calcium citrate malate is administered during the rest period.

A preferred method for the treatment of osteoporosis includes an initial diagnostic step, to determine the presence of the disorder. Thus, a preferred method of this invention comprises the steps of performing a diagnostic on a human subject for the detection of osteoporosis and, upon obtaining a positive result from said diagnostic, administering to said subject a safe and effective amount of calcium citrate malate for a period of time sufficient to build bone in said subject.

Suitable diagnostics for the detection of osteoporosis are well known in the art. Such methods include the measurement of the radiodensity of skeletal radiographs, quantitative computerized tomography, single energy photon absorptiometry, and dual-energy photon absorptiometry. Diagnostic techniques among those useful herein are described in W. A. Peck et al., *Physician's Resource Manual on Osteoporosis* (1987), published by the National Osteoporosis Foundation (incorporated by reference herein).

The following non-limiting examples illustrate the compositions, processes and uses of the present invention.

EXAMPLE I

An elderly human male subject, suffering from osteoporosis, is treated by a method of this invention. Specifically, a composition is prepared containing calcium citrate malate having a molar calcium:citrate:malate composition of about 6:2:3. The calcium citrate malate is made by first dissolving approximately 384.2 grams of citric acid and approximately 402.3 grams of malic acid in approximately 2 liters of water. This citrate/malate solution is then heated to approximately 55° C. (131° F.), with stirring. Separately, approximately 600.6 grams of calcium carbonate is added to approximately 1.2 liters of water, forming a slurry, with stirring.

The citrate/malate solution is then removed from its heat source, and the calcium carbonate slurry is added slowly, with stirring. The rate of addition is controlled, to contain the reaction as carbon dioxide is released. An additional quantity of water, approximately 0.4 liters, is finally added. The reaction mixture is then stirred for approximately 1 to 1.5 hours. The reaction is essentially complete as the pH of the solution equilibrates to approximately 4.3.

A precipitate of calcium citrate malate is thus formed. The excess reaction liquid is filtered off. The calcium citrate malate is dried, for approximately 12 hours at approximately 105° C. (221° F.), reducing the moisture level to less than about .1%. The dried product is then milled to approximately 10–20 mesh size, for a swallowable tablet formulation.

The swallowable tablet dosage form is then made, comprising:

| Component | % (by weight) |
| --- | --- |
| calcium citrate malate* | 99.73 |
| magnesium stearate | 0.27 |

*having a molar calcium:citrate:malate composition of approximately 6:2:3, made as described above in this Example.

The tablet formulation is made by thoroughly admixing the powders, and tabletting using a standard tablet press, to form tablets weighing approximately 1104 milligrams. The tablets are then coated, using a pan coater. The coating solution contains approximately 11% hydroxypropylmethyl cellulose, approximately 2% polyethylene glycol, approximately 3.5% colorant, and the balance of water.

The mass of the subject's thoracic vertebrae is determined by dual-energy photon absorptiometry. The human subject is then administered 4 of the tablets, comprised as above, each day for three months. The mass of the subject's vertebrae is then remeasured, indicating an increase in bone mass.

EXAMPLE II

A human female subject, suffering from postmenopausal osteoporosis, is treated by a method of this invention. Specifically, a beverage composition is prepared containing calcium citrate malate. The beverage is made comprising:

| Component | % (by weight) |
| --- | --- |
| 65° Brix Orange Juice Concentrate | 38.010 |
| aqueous orange essences | 10.099 |
| orange pulp | 4.958 |
| orange oils | 0.037 |
| orange flavor mix | 0.257 |
| calcium carbonate | 1.065 |
| citric acid | 1.249 |
| malic acid | 0.992 |
| sucrose | 16.710 |
| water | 26.623 |

A premix solution is prepared by dissolving the sugar and then the acids (citric and malic) in the water. Calcium carbonate is added and the mixture agitated until foaming ceases. This premix solution has a calcium to citrate/malate molar ratio of approximately 1:1.31, and a citric acid:malic acid molar ratio of approximately 1:1.14. The premix solution is added, with stirring, to the 65° Brix orange juice concentrate, followed by the orange essences, orange pulp, orange oil, and orange flavor mix. The resulting calcium-supplemented orange concentrate nectar has a sugar content of 42° Brix, 0.44% by weight calcium, calcium to citrate/malate molar ratio of approximately 1:2.38, and a citric acid:malic acid molar ratio of 1:0.71.

This concentrated beverage is then diluted, one part concentrate with three parts water, to form a single strength orange nectar beverage in drinkable form. When diluted, the beverage contains 60% orange juice and 0.11% by weight calcium.

The density of the human subject's vertebrae is measured by computerized tomography. Thereafter, the subject is administered approximately 180 milliliters (6 ounces) of the beverage composition (containing approximately 195 milligrams of calcium), per day, for one year. The vertebral mass of the subject is then remeasured, "indicating an increase in bone density."

EXAMPLE III

A human male subject, suffering from secondary osteoporosis as a result of a partial gastrectomy, is treated by a method of this invention. Specifically, a chewable tablet composition is administered to the subject, comprised as set forth below.

| Component | % (by weight) |
| --- | --- |
| calcium citrate malate* | 46.94 |
| mannitol | 46.69 |
| magnesium stearate | 0.68 |
| flavorant | 5.69 |

*having a molar calcium:citrate:malate composition of approximately 5:2:2, made in a manner analogous to that described in Example I, above.

The tablets are made by thoroughly admixing the powders, and tabletting on a standard tablet press, forming tablets weighing approximately 1844 milligrams. Each tablet contains approximately 250 mg of calcium (on an elemental basis).

The bone density of the subject's hip is measured by dual-energy photon absorptiometry. The subject is then administered 2 of the tablets, comprised as above, each day for six months. The bone density of the subject's hip is then remeasured, indicating an increase in the bone mass.

What is claimed is:

1. A method, for the building of bone in a human or other animal subject, comprising administering to said subject a safe and effective amount of calcium citrate malate for a sufficient period of time to build bone in said subject.

2. A method, for the building of bone according to claim 1, wherein said calcium citrate malate is administered at a level of from about 250 milligrams to about 1500 milligrams (on an elemental calcium basis), per day.

3. A method, for the building of bone according to claim 2, wherein said period of time is at least about three months.

4. A method, for the building of bone according to claim 1, wherein said calcium citrate malate has a molar ratio of citrate:malate of from about 1:0.5 to about 1:4.5.

5. A method, for the building of bone according to claim 4, wherein said calcium citrate malate has a molar ratio of citrate:malate of from about 1:0.75 to about 1:3.

6. A method, for the building of bone according to claim 4, wherein said calcium citrate malate has a molar ratio of calcium:total moles citrate plus malate of from about 1:0.7 to about 1:0.9.

7. A method, for the building of bone according to claim 6, wherein the equivalents of calcium in said calcium citrate malate is about equal to the total number of equivalents of citrate plus the equivalents of malate in said calcium citrate malate.

8. A method, for the building of bone according to claim 1, wherein said calcium citrate malate is in a solid dosage form.

9. A method, for the building of bone according to claim 1, wherein said calcium citrate malate is in a liquid dosage form.

10. A method, for the building of bone according to claim 9, wherein said dosage form is a juice-containing beverage.

11. A method of treating a human subject suffering from primary osteoporosis, according to claim 1.

12. A method of treating a human subject suffering from secondary osteoporosis, according to claim 1.

13. A method of treating a human subject suffering from bone fracture, according to claim 1.

14. A method, for the building of bone in a human or other animal subject in need thereof, comprising administering to said subject calcium citrate malate at a level of from about 250 milligrams to about 1500 milligrams, on an elemental calcium basis, for a period of time of at least about 3 months sufficient to build bone in said subject.

15. A method, for the building of bone according to claim 14, wherein said period of time is sufficient to increase the net skeletal mass of said subject by at least about 0.5%.

16. A method for the treatment of primary osteoporosis, according to claim 14.

17. A method, for the treatment of osteoporosis in a human or other animal subject, comprising administration to said subject calcium citrate malate at a level of from about 250 milligrams to about 1500 milligrams, on an elemental calcium basis, for a period of time sufficient to obtain a net skeletal mass that is clinically determined to be above the fracture threshold for said subject.

* * * * *